United States Patent [19]
Storch

[11] 3,982,530
[45] Sept. 28, 1976

[54] PENIAL APPLIANCE
[76] Inventor: Egon Storch, 98-19 64th Ave., Forest Hills, N.Y. 11374
[22] Filed: Apr. 22, 1975
[21] Appl. No.: 570,527

[52] U.S. Cl. ............................................... 128/79
[51] Int. Cl.² ........................................... A61F 5/00
[58] Field of Search ............... 128/79, 68.1, 87 R, 128/87 A

[56] References Cited
UNITED STATES PATENTS

| | | | |
|---|---|---|---|
| 844,798 | 2/1907 | Hawley | 128/79 |
| 1,144,103 | 6/1915 | Brant | 128/87 A |
| 1,417,414 | 5/1922 | Sanders | 128/87 A |

FOREIGN PATENTS OR APPLICATIONS

| | | | |
|---|---|---|---|
| 385,665 | 12/1923 | Germany | 128/79 |
| 432,290 | 1/1927 | Germany | 128/79 |
| 368,352 | 3/1923 | Germany | 128/79 |

*Primary Examiner*—Lawrence W. Trapp
*Attorney, Agent, or Firm*—David Fink

[57] ABSTRACT

A penial appliance for use in connection with a male organ of a person, featuring a base and a plurality of spaced apart elongated members extending from the base and defining an enclosure adapted to engage the male organ with the tips of the members engaging the body of the person, the enclosure having a length at least as long as the male organ.

7 Claims, 6 Drawing Figures

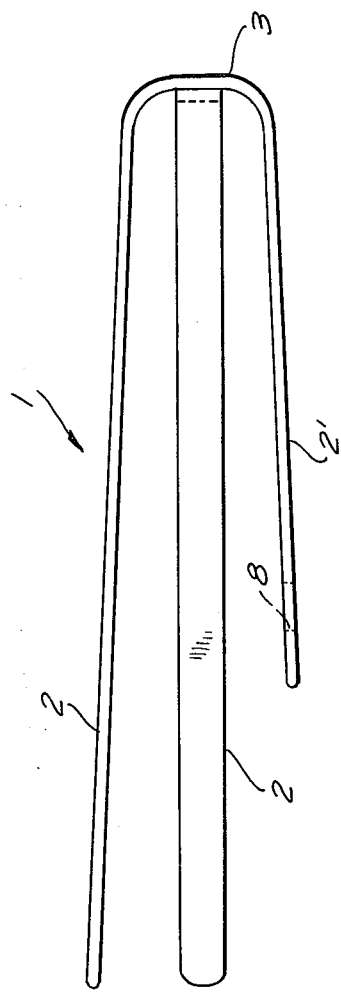
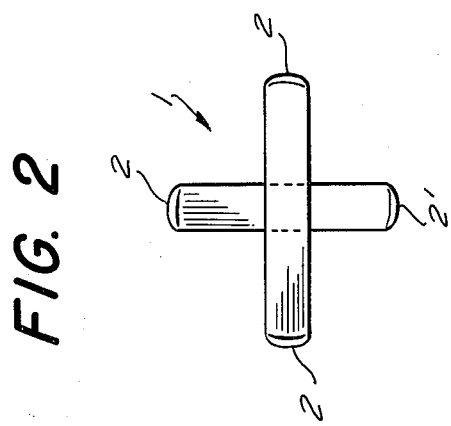
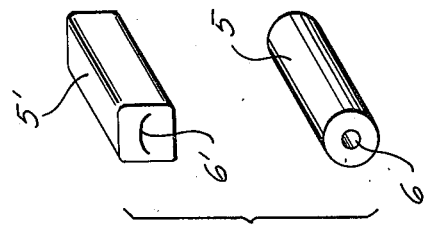
FIG. 1
FIG. 2
FIG. 3

PENIAL APPLIANCE

BACKGROUND OF THE INVENTION

The present invention relates to a penial appliance, and particularly to such appliance for enabling a male afflicted by partial or total impotence to engage in the performance of sexual intercourse.

DESCRIPTION OF THE PRIOR ART

There are generally three known types of penial appliances. The first is the implant type, such as shown in Strauch U.S. Pat. No. 3,853,122. This patent discloses a device which essentially comprises a flexible tube implanted in the penile shaft and an internal reservoir of fluid associated therewith whereby fluid can be displaced into the tube to render the tube relatively rigid so that a penile erection is achieved.

A second type of penile appliance is the blood flow pressure type, such as illustrated in the Jones U.S. Pat. No. 3,820,533. This device is an inflatable tubular member for externally encasing the penis which applies pressure to the penis to achieve and maintain an erectile condition by reducing the outflow of blood from the organ.

The third type of known penile appliance is the splint type to which the present invention pertains. Examples of this type are shown in U.S. Pat. Nos.: Hawley 844,798; Scheinkman 1,270,880; Renois 1,346,463; Huff 1,585,861; Scott 3,131,691 and Walters 3,495,588. These devices are relatively rigid members applied externally to the male organ to hold it extended with sufficient rigidity to achieve penetration of the female genitalia for performance of the sex act. Devices of this type are generally elongated members applied to the male organ as a surgical splint to provide a mechanical substitute for the erectile tissue of a normal organ. Some means are provided to retain the splint in position on the penis during copulation or at least during the initial stages of sexual intercourse.

The device for Hawley U.S. Pat. No. 844,798 is most closely related to the present invention in that it comprises an apertured base portion from which extends two longitudinal supporting members terminating in an open free end. This device has an elastic sheath attached to the base portion which is unrolled to encase the members to retain it on the male organ when the latter is positioned with the glans penis projecting through the aperture in the base and with the supporting members jacketing the shaft of the penis. An outwardly projecting flange is provided on the free end of each of the support members for forming abutments which rest against the body of the wearer.

SUMMARY OF THE INVENTION

The present invention is a splint type penial appliance which has a plurality of elongated support members of sufficient length to enclose fully the penis and provide sufficient rigidity to enable the performance of sexual intercourse. Abutment members are provided at the free end of the support members to supply a base for anchoring the device against the pubic bone of the wearer. The support members or ribs are formed from relatively rigid material which can nevertheless be easily cut to adjust the length of the device to permit enclosure of the entire length of the penis and anchorage of the free end against the body and to maintain such position despite any longitudinal or lateral expansion of the penis during use of the device. To facilitate adjustment of the length of the ribs the abutment members are readily removable from the ends of the ribs and may be replaced when desired.

The splint type devices which permit the penis to extend through the other end may cause severe discomfort during use when lateral expansion of the penis, the degree of which is completely unpredictable, causes pressure to be applied thereto at the aperture. This disadvantage of the prior art devices is avoided with the present invention by totally encasing the male organ.

An outer elastic retaining means is provided to maintain sufficient contact by the ribs with the penile shaft during use of the device, and such means is preferably a thin band of elastic material applied around the end of the device near the abutment members.

It should be noted that the present device can be worn by a male wearing a catheter by curling up the protruding rubber portion of the catheter between the tip of the penis and the inside surface of the outer end of the device.

Further, the present device may be used by a male with a unilateral inguinal hernia by adjusting the length of one or more ribs to avoid contact with the effected scrotal area.

It is an object of this invention to provide a penile appliance which is simple, efficient, and inexpensive to manufacture and which is easily and quickly applied when desired.

Other objects of the invention will emerge from the description which follows.

BRIEF DESCRIPTION OF THE DRAWINGS

FIG. 1 is a plan view of one embodiment of the penile appliance.
FIG. 2 is an end view of the device of FIG. 1.
FIG. 3 is a perspective view of the abutment means.

DESCRIPTION OF THE PREFERRED EMBODIMENT

Figure 4:
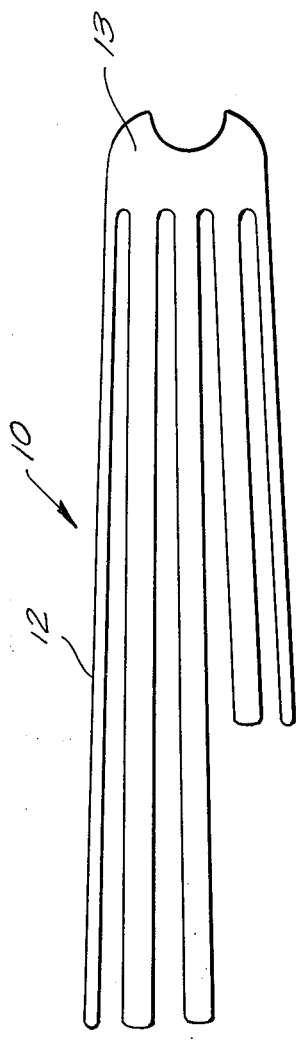
FIG. 4 is a plan view of another embodiment of the penile appliance.
Figure 5:
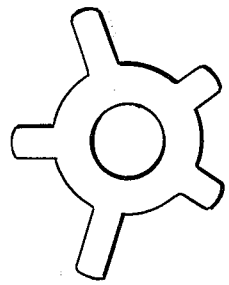
FIG. 5 is an end view of the device of FIG. 4.
Figure 6:
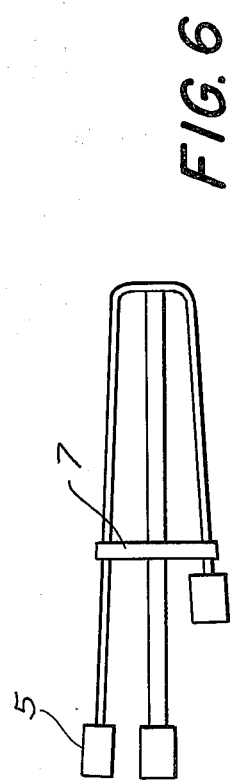
FIG. 6 is a schematic view of the assembly.

Referring to FIG. 1 of the drawings, the penile appliance designated generally 1 comprises four ribs or narrow elongate supporting members 2 terminating at a closed base portion 3 and extending therefrom in spaced apart relationship to each other to an open free end. The ribs 2 are formed from a thin relatively rigid material such as a plastic or metal sheet with a plastic coating. Such metal may be aluminum or stainless steel. The plastic or plastic coating may be a flexible elastomer, such as polyethylene, polypropylene, nylon plasticized polyvinylchloride, and the like. The thickness of the ribs and the hardness of the material is selected to enable the ribs to be cut with ordinary shears for adjusting the length of the ribs as will be hereinafter explained.

There are four ribs 2 extending from closed end 3. These ribs 2 may be formed by attaching together four elongated sections of the support material at the closed end, or may be formed by bending over the two elongate sections which are positioned to cross at right angles at their approximate midpoints. The ribs 2 are integrally connected at the closed end 3. One rib 2' is shorter than the others. During use of the device the shorter rib 2' is positioned along the underside of the penis so that no contact is made with the peno-scrotal junction to avoid discomfort in this area.

The free ends of the ribs may be curved, such as shown to avoid sharp edges.

FIG. 2 shows the splint structure 1 looking into the device from the left of FIG. 1. The ribs 2 extend at a slight angle outwardly from the longitudinal axis of the device, and converge toward their crossing points at the closed end 3. The ribs 2 are flexible and upon use of the device the ribs may be bent inwardly to grip the entire length of the penis by merely exerting manual pressure on the exterior surface of the ribs 2.

The ribs 2 may be readily cut to enable the length of ribs to be adjusted so that the free ends are positioned immediately adjacent the pubic bone of the wearer while the tip of the penis is located within and at a comfortable distance from the closed end 3 of the device. This permits longitudinal expansion of the penis during use without causing discomforting contact with the end of the device while the open end of the device remains anchored at the pubic bone area.

In order for one to apply this device, the open end of the appliance is slipped over the penis, with the latter usually in a flaccid state, and is positioned to press against the pubic bone firmly.

An abutment 5 is provided at the free end of each rib 2 to cushion the pubic bone area of the wearer against the pressure of the device during its use. Each abutment 5 is formed from a flexible natural or synthetic rubber material or soft plastic and may be rectilinear or cylindrical. An opening 6 is formed longitudinally in the abutment, preferably only partway therethrough. The abutment is mounted on the end of the rib 2 by slipping the free end of the rib 2 into the opening 6 in the abutment 5. The abutment 5 is thus easily removable and replaceable. The opening is slightly smaller than width of the rib so that the abutment will be retained on the rib during use of the device by means of its own resilience.

In FIG. 3, a rectilinear abutment 5' is illustrated having a slit 6' forming the opening for mounting the abutment 5' on the end of rib 2. The shape of the abutments is not critical.

It may be necessary to adjust the length of the device to approximate the length of the penis of a prospective wearer. This may be done by shearing off a like length from the free end of each rib 2. The abutment 5, 5' would be removed from the rib 2 prior to the cutting operation and replaced thereafter. The abutments must be separable from the ribs to enable the length of the device to be adjustable which is an important feature of the present device.

An elastic band 7 is provided to assist in retaining the device 1 in contact with the penile shaft during use. This band 7 is positioned around the ribs 2 closely adjacent the abutments 5, 5'. The band 7 is a narrow strip of elastic material, and may be one piece or preferably split and provided with a quick connecting adjustable closure means at the ends thereof, such as a Velcro type fastener. When the device 1 is applied around the penis and the ribs are squeezed into gentle contact with the penile shaft, the band of elastic material 7 is positioned tightly around the ribs 2 to maintain engagement of the device with the penis during copulation.

A slot 8 may be provided in the shorter rib 2' through which extends the open band 7 of said elastic material. This retains the band 7 with the support structure during its application to a penis and avoids misplacement or mishandling of this relatively small component of the overall assembly.

Another embodiment of the penile appliance is shown in FIG. 4. This device 10 is provided with five longitudinally extending ribs 12 joined at a circular base portion 13 which may be apertured if desired as shown. However, it is to be understood that the length of the device is made to totally encase the penis, and the tip of the penis during use does not project through the aperture when provided. Such aperture may be provided only for ease of manufacture or for lightening the weight of the structure.

In this embodiment, two or more ribs 12' are shorter than the others to provide an area of reduced length for positioning in registry with the penal-scrotal junction. The ribs 12, 12' are formed integrally with the base portion 13 and extend therefrom at a slight angle outwardly from the longitudinal axis of the device 10. The end of each rib 12, 12' is rounded to facilitate mounting the abutment members thereon. A slot may be provided in one of the shorter ribs 12' for attaching the band of elastic material 7 to the support structure.

A typical penile appliance of this invention is approximately 6 inches in overall length with the shorter rib or ribs about 2 inches shorter than the others. The length of a typical abutment would be about ½ inch.

In the embodiment of FIG. 4 the ribs extend to about ½ inch from the end of the base portion.

The present disclosure includes that contained in the appended claims, as well as that of the foregoing description. Although this invention has been described in its preferred form with a certain degree of particularity, it is understood that the present disclosure of the preferred form has been made by way of example and that numerous changes in the details of construction and the combination and arrangement of parts may be resorted to without departing from the spirit and the scope of the invention as hereinafter claimed.

What is claimed is:

1. A penial appliance for use in connection with the male organ of a person comprising, in combination:
    a base:
    a plurality of spaced apart elongated members extending from said base and defining an enclosure adapted to engage said male organ with the tips of said members engaging the body of said person;
    said enclosure having a length at least as long as said male organ:
    said base forming a barrier to said male organ; and
    abutment means connected to the tips of said members against the body of said person is substantially non-irritating.

2. A penial appliance for use in connection with the male organ of a person comprising, in combination
    a base;
    a plurality of spaced apart elongated members extending from said base and defining an enclosure adapted to engage said male organ with the tips of said members engaging the body of said person,
    said enclosure having a length at least as long as said male organ; and
    abutment means connected to the respective tips of said members, whereby the engagement of the tips of said member against the body of said person is substantially non-irritating;
    at least one of said members being shorter than the others, whereby the engagement of said penial appliance in a position substantially orthogonal to the body is optimized.

3. The penial appliance as claimed in claim 2, further comprising retaining means operable to press said member against said male organ to maintain engagement therewith.

4. The penial appliance as claimed in claim 3, wherein said retaining means comprises an elastic band.

5. The penial appliance as claimed in claim 4, wherein at least one of said members includes an aperture defined therein and operable for engagement with said elastic band, whereby said elastic band is maintained connected to said penial appliance.

6. A penial appliance for use in connection with the male organ of a person comprising, in combination:
a base;
a plurality of spaced apart elongated members extending from said base and defining an enclosure adapted to engage said male organ with the tips of said members engaging the body of said person,
said enclosure having a length at least as long as said male organ; and
abutment means connected to the respective tips of said members, whereby the engagement of the tips of said member against the body of said person is substantially non-irritating;
said abutment means being removably connected to the tips of said members.

7. The penial appliance as claimed in claim 3, wherein said retaining means comprises a quick disconnect means having connected and disconnected states and operable for connecting and disconnecting said retaining means.

* * * * *